United States Patent [19]

Lin et al.

[11] Patent Number: 5,517,860

[45] Date of Patent: May 21, 1996

[54] FILM TESTING

[75] Inventors: Li Lin, Wallingford; Melvin H. Johnson, Chadds Ford, both of Pa.

[73] Assignee: E. I. Du Pont de Nemours and Company, Wilmington, Del.

[21] Appl. No.: 382,815

[22] Filed: Feb. 3, 1995

[51] Int. Cl.[6] .................................................. G01D 1/16
[52] U.S. Cl. .................................................. 73/789; 73/790
[58] Field of Search .................................. 73/7, 78, 789, 73/790, 791, 795

[56] References Cited

U.S. PATENT DOCUMENTS

| | | | |
|---|---|---|---|
| 4,140,008 | 2/1979 | Golembeck et al. | 73/78 |
| 4,342,227 | 8/1982 | Petersen et al. | 73/510 |
| 4,922,756 | 5/1990 | Henrion | 73/517 R |
| 5,074,983 | 12/1991 | Eltoukhy et al. | 73/7 |
| 5,255,562 | 10/1993 | Yamamoto et al. | 73/78 |
| 5,299,450 | 4/1994 | Nakagawa et al. | 73/78 |

FOREIGN PATENT DOCUMENTS 1765730  9/1990  U.S.S.R. .

OTHER PUBLICATIONS

Benecke, W., Silicon–microactuators: activation mechanisms and scaling problems, *Tansducers '91. 1991 International Conference on Solid–State Sensors and Actuators, Digest of Technical Papers*, Jun. 1991.

*Primary Examiner*—Richard Chilcot
*Assistant Examiner*—Max Noori
*Attorney, Agent, or Firm*—Hilmar L. Fricke

[57] ABSTRACT

Measurement of stress-strain relationships in thin films using substantially flat, parallel test surfaces with minimal width.

6 Claims, 3 Drawing Sheets

FILM TESTING

BACKGROUND OF THE INVENTION

A wide variety of techniques have previously been used in the measurement of mechanical properties of thin films. These techniques include miniature tension, bulge test, nano- or micro-indentation and microbeam deflection. Tensile tests measure in-plane properties of thin films. However, the in-plane properties can be different from out-of-plane properties, and it is the latter which are often more relevant to the performance of the films in their intended applications. In addition, tensile experiments impose tensile stresses on samples, which promote fracture failure earlier in the deformation, and may mask observations of plastic flow. In addition, areas supporting the load in tensile tests decrease as loads increase, leading to instability with necking and non-uniform straining. As a result, large-strain properties cannot be obtained front tensile tests.

Representative of previous tensile tests is bulge testing, which is a biaxial tensile test. There, both stresses and strains can only be roughly estimated through mathematical modeling because of the complex geometry of deformation.

Microindentation testing is a widely-used technique to study the mechanical properties of thin films. While simple in operation, expensive equipment has been required, and the non-uniform deformation results in complicated stress and strain fields, and also makes understanding and interpreting the measurements difficult. Even with the help of sophisticated computational models, no stress-strain relationships can be extracted from microindentation measurements.

SUMMARY OF THE INVENTION

The present invention provides an improved testing apparatus and method which enables uniform measurement of stress-strain relationships for thin films in the out-of-plane direction to large strain deformation.

Specifically, the present invention provides, in a testing apparatus comprising means for determining the stress-strain relationship in a film of polymeric material to produce an electronic signal, and means for converting the electronic signal to visual or graphic form, the improvement wherein the means for determining the stress-strain relationship comprises:

(a) first and second substantially flat test surfaces between which the film is placed for testing, the flat test surfaces each having a substantially linear configuration and in substantially complete alignment and wherein the width of each test surface is at least equal to the thickness of the film and no greater than twice the thickness of the film;

(b) means for positioning the test surfaces substantially parallel to each other; and (c) means for moving one of the test surfaces with respect to the second test surface.

DETAILED DESCRIPTION OF THE INVENTION

The present invention is applicable to the measurement of properties in thin films. Thin films, as used herein, are understood to mean unsupported planar structures having a thickness of about from 1 to 1000 microns.

A central element of the present invention is the provision of two substantially flat test surfaces between which the film is placed for testing, means for positioning the test surfaces substantially parallel to each other and in alignment, and means for deforming a sample.

The test surfaces used in the present invention are substantially flat and substantially parallel. By substantially flat is meant that the surface variation of the width of the anvil is less than about 30 nm. Test surfaces having the required degree of flatness can be prepared from a variety of materials. However, silicon has been found to be particularly satisfactory because of its crystalline structure. By forming the test surface, or anvil, from a single crystal, an exceptionally high degree of flatness can be obtained, since such surfaces can be a crystallographic plane, and accordingly flat on the atomic level. Silicon also has excellent mechanical properties, and exhibits substantially no hysterysis. In addition, because of its anisotropic properties, silicon can be micromachined with great precision. An additional important element of the present invention is that the upper and lower anvils be substantially in alignment. Specifically, any misalignment between the two anvils should generally be less than about 2 microns. Alignment can be measured, for example, according to the techniques described in detail in Johnson et al. U.S. Pat. No. 5,377,289.

The flat test surfaces are basically knife-like in configuration, but the test surface, or anvil, is flat rather than a cutting edge. Accordingly, the test surfaces are said to have a substantially linear configuration. The width of each test surface is at least equal to the thickness of the film being tested, and no greater than twice the thickness of the film. Within this range, edge effect and the effect of surface friction in the testing have little influence on the test results.

The width of the sample is preferably substantially greater than the width of the anvil. This assures that the deformation will be two-dimensional.

The substantially parallel configuration of the test surfaces can be obtained by the preferred double cantilever design. Using such a construction, the integral anvils can be positioned parallel before and during the test period. The cantilever beams can be prepared from a variety of materials. However, a unitary structure of silicon is similarly preferred for the beams.

Figure 1:
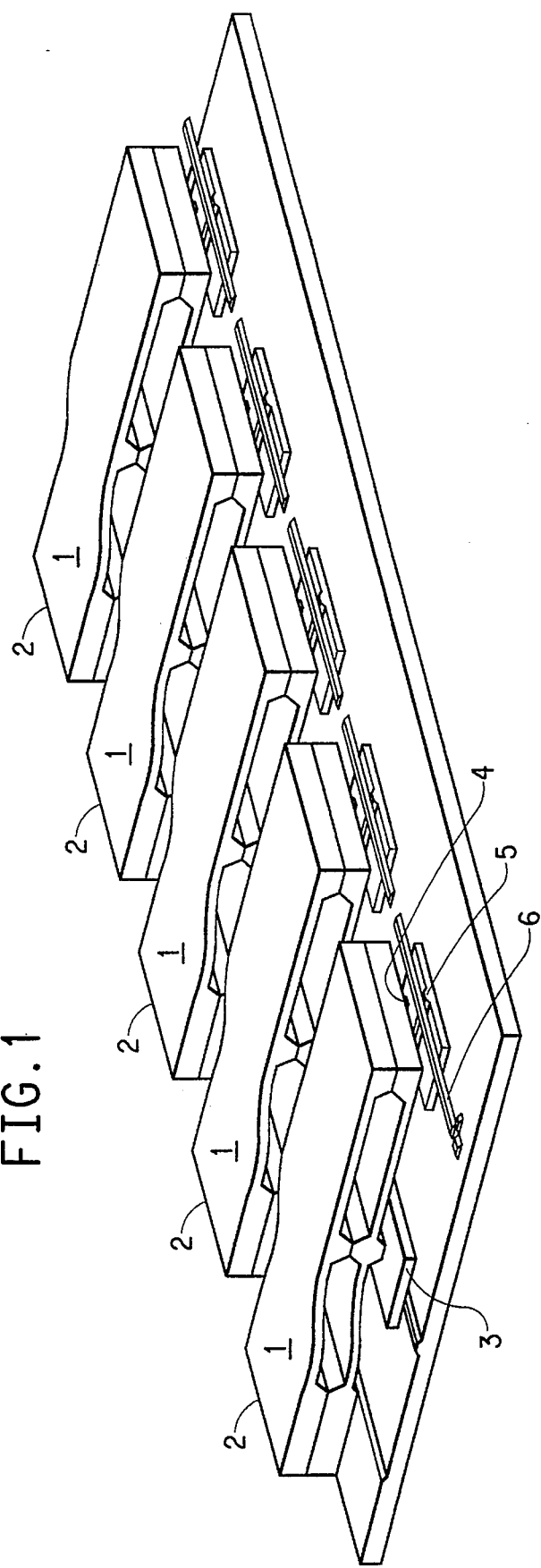
FIG. 1 is a schematic representation of an apparatus of the present invention.

The invention will be more fully understood by reference to the drawings, in which FIG. 1 is a schematic perspective view of an apparatus of the invention. There, double cantilevered beams 1, anchored at their proximal ends 2, are positioned over shims 3. Anvils 4 and 5 are integral with the distal ends of the beams, and positioned to impinge on sample 6. In this illustration, a single, continuous sample is used for all testing surfaces. However, separate samples for each test surface can also be used.

Figure 2:
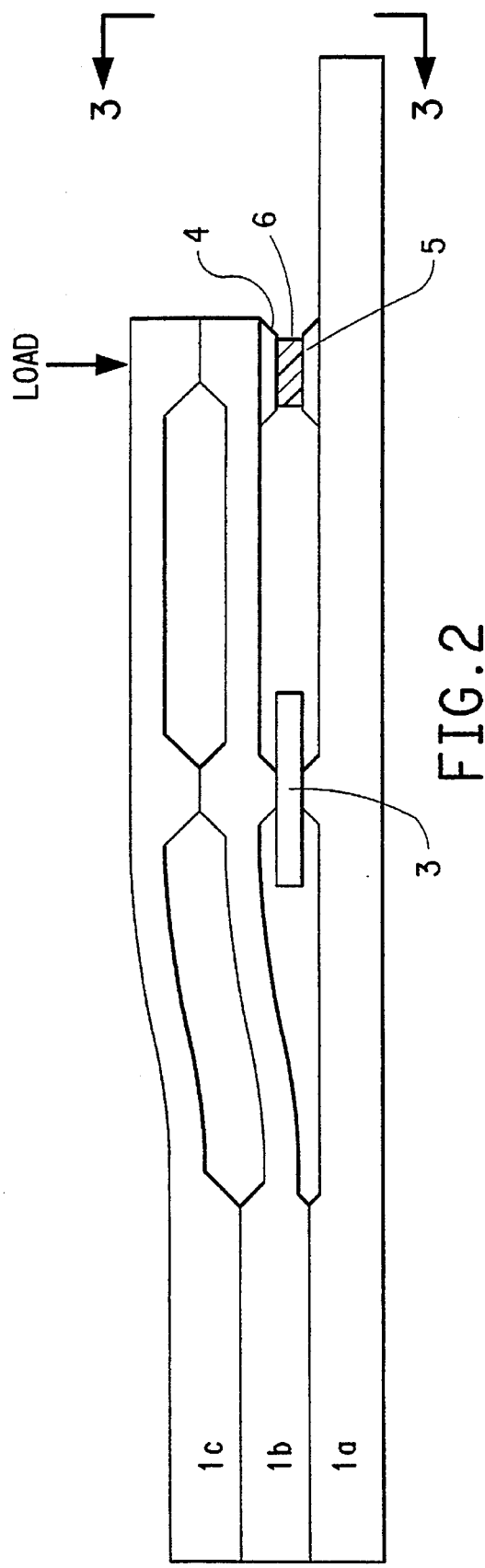
FIG. 2 is a cross-sectional schematic representation of a detail of an apparatus of the invention.
Figure 3:
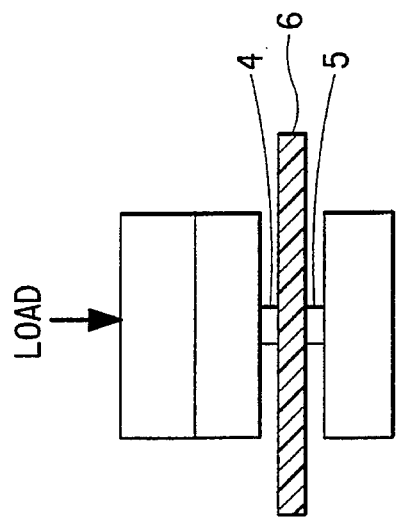
FIG. 3 is a view of a portion of the apparatus, taken at a right angle to FIG. 2.

As shown more clearly in FIG. 2, the double cantilevered beans are typically composed of base 1a, middle portion 1b, and upper portion 1c. These portions, preferably fabricated from a unitary crystal as discussed above, can be formed into the desired configuration by customary microfabrication techniques, as are well known to those skilled in the art. In the course of such fabrication, the anvil portions which come into contact with the sample are formed. After microfabrication, the components of the cantilever beam are assembled by suitable techniques such as fusion bonding. As illustrated more clearly in FIG. 3, the anvil has a substantially linear configuration, and the cross-section of the anvil is rectilinear, to provide the flat surface which comes into contact with the sample.

The shims used to aid in the parallel alignment of the two test surface can be prepared from a wide variety of materials, which can be the same or different than the material from which the cantilever is prepared. It has been found particularly satisfactory, however, to use shims prepared from metal or metal alloys such as stainless steel.

Figure 4:
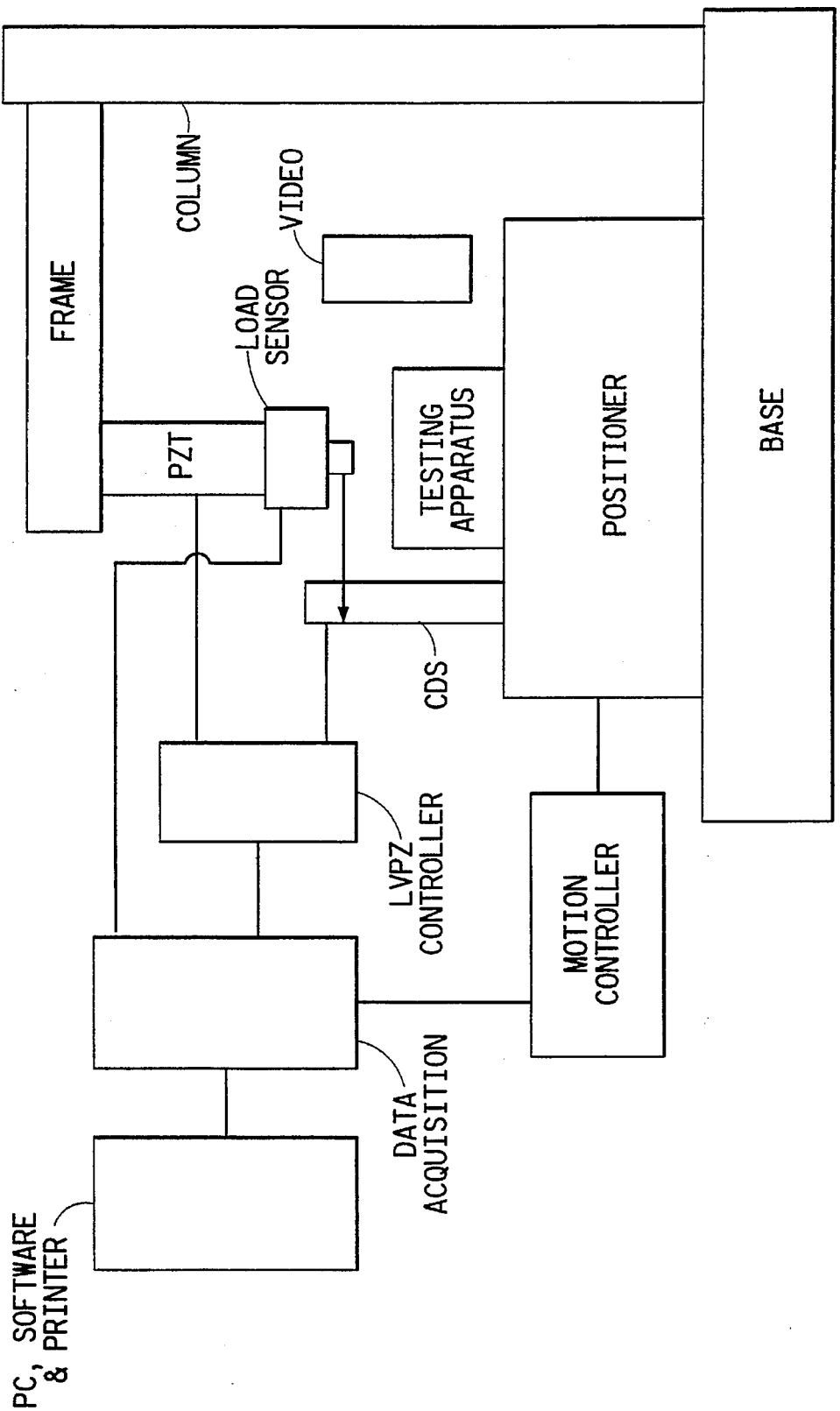
FIG. 4 is a schematic representation of the components used for converting the electronic signals generated in the course of the testing to visual or graphic form.

FIG. 4 illustrates the operation of the apparatus. An upper test surface is displaced, by the piezo translator, to contact and deform the sample within the testing apparatus. For accurate measurement of the properties of thin samples, the movement of the test surface or anvil should be carefully controlled, to permit recording of changes of as little as one nanometer. The overall apparatus and method comprise conventional components selected to provide the precise control of motion and measurement of the deformation. Such a driving and probing system can include, for example, commercially available apparatus of the types noted.

The displacement is measured by a capacitive displacement sensor (CDS), and the resulting electronic signal is transmitted to the low voltage piezo controller to form a closed loop control. The force required for the deformation is measured by the load sensor to produce an electronic signal, along with the displacement of the test surface. The load sensor measures the resistance of the thin film sample to the test load. The electronic signals from the load sensor and the CDS are collected by the Data Acquisition board, which converts the analog signals to digital signals. These signals, in turn, are transmitted to the computer memory for storage, display and processing.

The running time of the test depends on the rate of deformation of the sample, but is normally completed within ten minutes. Software can be programmed to create a step change in the rate of deformation. During the test, the deformation is computer controlled, with a feedback loop that assures precision application of accurately measured displacement. Force is measured through a mode sensor simultaneously. The information is fed directly into a computer where the information is recorded. The program monitors and measures the amount of force at displacement. The data can be analyzed immediately or stored for later review. This makes it possible to take measurements of a series of samples at the same time, permitting the data analysis at a later time. Similarly, a change of the rate of deformation during the test procedure provides additional information about the behavior of the sample during the changes in conditions.

The load displacement data is corrected for system stiffness and compliance of the anvil, and then converted to a stress-strain curve in an appropriate form.

The instant invention is applicable to a wide variety of thin film materials, including coating materials such as those used, for example, in automotive applications, and various polymeric films, such as polyolefins, polyamides, polyimides and polyesters, as well as spunbonded sheets.

The present invention provides a flexible and adaptable means for the study of the intrinsic mechanical properties of thin film materials, providing the ability to quickly and accurately determine the properties that effect performance of the materials in thin film form. The uniform deformation of the samples in the present invention, through the use of the flat test surfaces, their size, parallel arrangement and alignment, permits precise measurement of deformation and calculation of the stress-strain relationship.

We claim:

1. In a testing apparatus comprising means for determining the stress-strain relationship in a film of polymeric material to produce an electronic signal, and means for converting the electronic signal to visual or graphic form, the improvement wherein the means for determining the stress-strain relationship comprises:

(a) first and second substantially flat test surfaces between which the film is placed for testing, the flat test surfaces each having a substantially linear configuration and in substantially complete alignment and wherein the width of each test surface is at least equal to the thickness of the film and no greater than twice the thickness of the film;

(b) means for positioning the test surfaces substantially parallel to each other; and (c) means for moving one of the test surfaces with respect to the second test surface;

wherein the means for positioning at least one of the test surfaces is a double cantelever structure onto which one test surface is attached.

2. An apparatus of claim 1 wherein each test surface has a surface variation of less than about 30 nm.

3. An apparatus of claim 2 wherein each of the test surfaces comprises a single crystal.

4. An apparatus of claim 3 wherein at least one of the test surfaces consists essentially of silicon.

5. In a method for determining the stress-strain relationship in a film of polymeric material to produce at least one electronic signal reflecting the resistance of a sample to compressive deformation, and converting the electronic signal to visual or graphic form, the improvement wherein the stress-strain relationship comprises:

(a) placing the film between first and second substantially flat test surfaces for testing, the flat test surfaces each having a substantially linear configuration and wherein the width of each test surface is at least equal to the thickness of the film and no greater than twice the thickness of the film;

(b) positioning the test surfaces substantially parallel to each other; and (c) moving one of the test surfaces toward second test surface to compress the film; and (d) measuring the force required to compress the film wherein the test surfaces are positioned substantially parallel by means of a double cantelever structure onto which one test surface is attached.

6. A method of claim 5 wherein each test surface has a surface variation of less than about 30 nm.

\* \* \* \* \*